United States Patent [19]
Fuisz

[11] Patent Number: 6,129,926
[45] Date of Patent: Oct. 10, 2000

[54] FLASH FLOW PROCESSING OF THERMOPLASTIC POLYMERS AND PRODUCTS MADE THEREFROM

[75] Inventor: Richard C. Fuisz, Great Falls, Va.

[73] Assignee: Fuisz Technologies Ltd., Chantilly, Va.

[21] Appl. No.: 08/074,863

[22] PCT Filed: May 13, 1992

[86] PCT No.: PCT/US92/04053

§ 371 Date: Oct. 29, 1993

§ 102(e) Date: Oct. 29, 1993

[87] PCT Pub. No.: WO92/20330

PCT Pub. Date: Nov. 26, 1992

Related U.S. Application Data

[63] Continuation-in-part of application No. 07/702,068, May 17, 1991, abandoned.

[51] Int. Cl.$^7$ .............................. A61K 9/70; A61K 31/00
[52] U.S. Cl. .............................. 424/401; 424/2; 424/443; 424/76.1; 424/489
[58] Field of Search .............................. 424/401, 2, 443, 424/489, 76.1

[56] References Cited

U.S. PATENT DOCUMENTS

| | | |
|---|---|---|
| 2,826,169 | 3/1958 | Le Veen . |
| 2,918,404 | 12/1959 | Mende . |
| 3,019,745 | 2/1962 | Du Bois . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,118,396 | 1/1964 | Brown et al. . |
| 3,131,428 | 5/1964 | Mika . |
| 3,308,221 | 3/1967 | Opfell . |
| 3,324,061 | 6/1967 | Tanquary et al. . |
| 3,482,998 | 12/1969 | Carroll et al. . |
| 3,523,889 | 8/1970 | Eis . |
| 3,557,717 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,676,148 | 7/1972 | De Weese et al. . |
| 3,686,000 | 8/1972 | Lawrence . |
| 3,723,134 | 3/1973 | Chivers . |
| 3,762,846 | 10/1973 | Chivers . |
| 3,766,165 | 10/1973 | Rennhard . |
| 3,856,443 | 12/1974 | Salvi . |
| 3,875,300 | 4/1975 | Homm et al. . |
| 3,876,794 | 4/1975 | Rennhard . |
| 3,925,525 | 12/1975 | La Nieve . |
| 3,930,043 | 12/1975 | Warning et al. . |
| 3,951,821 | 4/1976 | Davidson . |
| 3,967,623 | 7/1976 | Butterworth et al. . |
| 3,972,725 | 8/1976 | Nicol . |
| 3,981,739 | 9/1976 | Dmitrovsky et al. . |
| 3,992,265 | 11/1976 | Hansen . |
| 4,056,364 | 11/1977 | Dmitrovsky et al. . |
| 4,072,658 | 2/1978 | Okamoto et al. . |
| 4,086,418 | 4/1978 | Turbak . |
| 4,090,920 | 5/1978 | Studer, Jr. . |
| 4,136,145 | 1/1979 | Fuchs et al. . |
| 4,153,512 | 5/1979 | Messner et al. . |
| 4,159,210 | 6/1979 | Chen et al. . |
| 4,293,570 | 10/1981 | Vadasz . |
| 4,303,684 | 12/1981 | Pitchon et al. . |
| 4,335,232 | 6/1982 | Irwin . |
| 4,338,350 | 7/1982 | Chen et al. . |
| 4,348,420 | 9/1982 | Lynch et al. . |
| 4,362,757 | 12/1982 | Chen et al. . |
| 4,371,516 | 2/1983 | Gregory et al. . |
| 4,376,743 | 3/1983 | Dees . |
| 4,382,963 | 5/1983 | Klose et al. . |
| 4,492,685 | 1/1985 | Keith et al. . |
| 4,496,592 | 1/1985 | Kuwahara et al. . |
| 4,500,546 | 2/1985 | Turbak et al. . |
| 4,511,584 | 4/1985 | Percel et al. . |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0 287 488 A1 | 3/1988 | European Pat. Off. . |
| 0 387 950 A1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 489211 | 4/1971 | Switzerland . |
| 519858 | 4/1971 | Switzerland . |
| 2 155 934 B | 3/1985 | United Kingdom . |
| WO 91/18613 | 5/1991 | WIPO . |

OTHER PUBLICATIONS

R.H. Doremus, "Crystallization of Sucrose From Aqueous Solution," *Journal of Colloid and Intereface Science*, 104, pp. 114–120 (1985).

P. Bennema, "Surface Diffusion and the Growth of Sucrose Crystals, " *Journal of Crystal Growth*, 3,4 pp. 331–334 (1968).

(List continued on next page.)

*Primary Examiner*—Raj Bawa
*Attorney, Agent, or Firm*—John F. Levis

[57] ABSTRACT

A method of producing a solid thermoplastic-containing matrix by flash flow processing thermoplastic polymers as well as the products produced by such method is provided. The method involves subjecting a feedstock of a thermoplastic polymer to flash flow melt spin processing at a temperature of about 200–430° F. and shear imposed by centrifugal force from an operating speed of about 3600–3800 rpm. The matrix thus prepared is in the form of a floss, fiber, flake, filament, ribbon, spicule and mixtures thereof A guest material such as a dye, a fragrance, a comestible, an oil, a photographic reducer and developer, an organism, an antioxidant and a medicament may further be incorporated into the feedstock prior to processing.

29 Claims, No Drawings

U.S. PATENT DOCUMENTS

| | | |
|---|---|---|
| 4,526,525 | 7/1985 | Oiso et al. . |
| 4,585,797 | 4/1986 | Cioca . |
| 4,619,833 | 10/1986 | Anderson . |
| 4,765,991 | 8/1988 | Cherukuri . |
| 4,772,477 | 9/1988 | Weiss et al. . |
| 4,793,782 | 12/1988 | Sullivan . |
| 4,855,326 | 8/1989 | Fuisz ........................................ 514/777 |
| 4,872,821 | 10/1989 | Weiss . |
| 4,873,085 | 10/1989 | Fuisz . |
| 4,879,108 | 11/1989 | Yang et al. . |
| 4,885,281 | 12/1989 | Hanstein et al. . |
| 4,978,537 | 12/1990 | Song . |
| 4,997,856 | 3/1991 | Fuisz . |
| 5,011,532 | 4/1991 | Fuisz . |
| 5,028,632 | 7/1991 | Fuisz . |
| 5,034,421 | 7/1991 | Fuisz . |
| 5,073,387 | 12/1991 | Whistler . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,173,322 | 12/1992 | Melachouris et al. . |
| 5,196,199 | 3/1993 | Fuisz . |
| 5,236,734 | 8/1993 | Fuisz . |
| 5,238,696 | 8/1993 | Fuisz . |
| 5,279,849 | 1/1994 | Fuisz . |
| 5,286,513 | 2/1994 | Fuisz . |
| 5,288,508 | 2/1994 | Fuisz . |
| 5,348,758 | 9/1994 | Fuisz et al. ............................. 426/660 |
| 5,456,932 | 10/1995 | Fuisz et al. ............................. 426/548 |
| 5,518,730 | 5/1996 | Fuisz ...................................... 424/426 |

OTHER PUBLICATIONS

T.D. Simpson, et al., "Crystalline Forms of Lactose Produced in Acidic Alcoholic Media,"*Journal of food Science*, 47, pp. 1948–1954 (1982).

A.D. Randolph, et al., "Continuous Sucrose Nucleation," *The International Sugar Journal*, pp. 8–12, 73–77 (1974).

K.B. Domovs, et al., "Methanol–Soluble Complexes of Lactose and of other Carbohydrates,"*J. Dairy Science*, 43, pp. 1216–1223 (1960).

A.D. Randolph, et al., "Continuous Sucrose Nucleation, "*The International Sugar Journal*, pp. 35–38 (1974).

ICI Americas Inc., "ICI Americas Products for Cosmetics and Pharmaceuticals," (1977).

FLASH FLOW PROCESSING OF THERMOPLASTIC POLYMERS AND PRODUCTS MADE THEREFROM

This application is a continuation-in-part application of U.S. application Ser. No. 702,068 which was filed May 17, 1991, now abandoned.

BACKGROUND OF THE INVENTION

The present invention relates to a new method for processing thermoplastic materials and the products thereby produced.

In U.S. Pat. No. 4,855,326, issued Aug. 8, 1989, various substances having pharmacological properties were combined with a sugar and spun into fibers to produce a readily water-soluble product. The various examples enumerated in the patent all involved the use of water-soluble medicaments and were directed to enhancing the solubility rate of the different substances. The patent describes methods for combining a medicament with any one or more of the water-soluble melt spinnable sugars and spinning the combination to produce a readily soluble floss form of the medicament. The '326 patent also discloses the use of polyvinylpyrrolidone dissolved in isopropyl alcohol combined as an adhesion promoter with granular sugar and a medicament. The combination was melt spun. The polymer, however, was present as a liquid and was used only as an additive. The disclosure of the '326 patent is incorporated herein by reference.

In U.S. Pat. No. 5,011,532, issued Apr. 30, 1991, the disclosure deals with oleaginous substances such as vegetable oil, baby oil, margarine, lanolin, cocoa butter, and the like, and how their lack of affinity for water is altered by mixing the oleaginous substance with sugar and melt spinning the mixture in a cotton candy spinning machine or the equivalent. As so modified the products disperse in water forming a colloidal or pseudo-colloidal dispersion. Such modification enabled such widely disparate procedures as: (a) incorporating shortening oil in a premixed cake mix containing flour but no egg to which water is added to produce a batter: and (b) producing a confection or medicated lozenge by dehydrating the dispersion and allowing the melted residue to solidify. The aforementioned application discloses that any oleaginous substance that can be mixed with a melt-spinnable sugar, when spun in a cotton candy spinning machine, produces a product which, when added to water or has water added to it, forms a uniform dispersion having all the appearances of a colloidal dispersion. In an example of the '532 patent, polyethylene glycol, mol. wt. 400, was combined with sucrose and subjected to melt spinning. However, the polymer was in liquid form and was present only as an additive. The disclosure of the '532 patent is incorporated herein by reference.

U.S. Pat. No. 4,496,592 to Kuwahara, et al. discloses a process for producing chewing gum which includes spinning gum base and sugar or candy in an ordinary candy floss making machine. The gum base used by Kuwahara, et al. can be natural or synthetic gum base prepared by a conventional method with other required ingredients. The sugar (or candy) ingredient is incorporated in an amount of from 66% to 83% by weight of the feedstock.

Other disclosures which relate to spinning substances with one or more sugars are found in U.S. Pat. No. 4,873,085 issued Oct. 10, 1989, U.S. Pat. No. 5,034,421 issued Jul. 23, 1991, U.S. Pat. No. 5,028,632 issued Jul. 2, 1991, and U.S. Pat. No. 4,997,856 issued Mar. 5, 1991. The products described in the above-mentioned patents and applications are all produced by processing in a cotton candy machine. Illustrative of a cotton candy machine is the Econo Floss Model 3017 manufactured by Gold Medal Products Co. of Cincinnati, Ohio. The process described in the above-identified disclosures involve the use of sugar(s) as a feedstock material which is spun to produce a material such as a floss, fibre, etc. Accordingly, the technology described in the above-identified disclosures relies on the physical characteristics of sugar.

In the parent of the present application, application Ser. No. 07/702,068, the U.S. Patent Office has cited other disclosures for their showing of melt-spinning polymers. U.S. Pat. No. 4,335,232 to Irwin was cited as disclosing melt-spinnable aromatic copolyesters, and U.S. Pat. No. 4,072,658 to Okamoto, et al. was cited for its disclosure of melt spinning polystyrene. However, the "melt-spinning" techniques referred to in the Irwin '232 and the Okamoto, et al. '658 disclosures are conventional "melt-spinning" techniques wherein the feedstock is subjected to sustained heat treatment.

Conventional, melt spinning techniques, such as those referred to by Irwin and Okamoto, et al., are described in F. Billmeyer Jr., *Text Book of Polymer Science*, 518–522 (Wiley International Edition, 2d). Spinning processes require melting the polymer or dissolving the polymer in solution (an exception is the aqueous dispersion of a polymer, such as polytetrafluoroethylene, followed by removal of the liquid and sintering). In the melt spinning procedure, molten polymer is pumped at a constant rate under high pressure through a plate having a number of small holes, which is referred to as a spinnaret. Polymer is melted, usually by contacting it with a hot grid or by use of an extrusion-type screw, and passed directly to a meter pump. Filaments emerge from the spinnaret into air where it begins to cool. As the fibers solidify, they are brought together and drawn to orient the fibers. In both dry spinning and wet spinning procedures, the polymer or polymer derivative is put into solution prior to forming the fiber.

The procedures disclosed in the prior art do not enable the artisan to alter a thermoplastic material quickly and efficiently to provide unique characteristics useful in a wide variety of applications. It is, therefore, a purpose of the present invention to provide a completely new method of processing thermoplastic material for a vast number of uses.

SUMMARY OF THE PRESENT INVENTION

The present invention is a unique method of producing a host thermoplastic material (as well as the products resulting therefrom) which includes subjecting a feedstock consisting essentially of a thermoplastic polymer to conditions of temperature and shear sufficient to induce flash flow which alters the physical and/or chemical structure of the feedstock. The term "host" as used herein means the majority of the resulting product after being subjected to the process of the present invention. Consequently, the matrix which results from the present process is composed of thermoplastic material which may or may not carry a guest material therein.

Thermoplastic material as used in the present invention means material which exhibits plasticity and can be molded when subjected to heating. The thermoplastic material can be selected from the group consisting of acrylonitrile-butadiene-styrene (ABS) resins; acetals; acrylics; cellulosics; chlorinated polyethers; fluorocarbons such as polytetrafluoroethylene (PTFE), polychlorotrifluoroethylenes (CTFE), and fluorinated ethylene propylene (FEP); nylons (polyamides); polycarbonates; polyethylene polymers and copolymers; polypropylene polymers and copolymers; polystyrenes; vinyls; and combinations thereof.

Flash flow is referred to in the present process as a phenomena which occurs when a solid carrier material (e.g., thermoplastic material) is subjected to conditions of temperature and shear sufficient to provide internal flow at a subparticle level. This condition produces a transformation of physical and/or chemical structure without degradation of the material. Internal flow occurs when the infrastructure of the material breaks down sufficiently to permit movement of the material at a subparticle level, and probably at a molecular level. At a molecular level, internal flow contemplates the movement of molecules relative to each other.

In the present invention, thermoplastic material is subjected to flash flow sufficiently to deform and pass through an opening under minimum amount of force. The force used in the present preferred embodiments of the invention is centrifugal force provided by a spinning head from which the deformed flowable material is thrown at high speed. No external force is imposed on the flowable thermoplastic material after it is flung out of the spinning head. The thermoplastic material instantaneously reforms as a solid having altered physical and/or chemical structure. The altered structure results from the forces acting on the material as it exits the head and is hurled outwardly during the brief period during which it experiences flash flow.

The flash flow phenomena of the present invention occurs in not more than one second, preferably on the order of tenth of seconds, e.g., not more than about 0.4 seconds, and most preferably on the order of milliseconds and certainly not more than 0.1 second. This unique phenomena can be produced by relatively high speed distribution of the thermoplastic material to an environment of elevated temperature under a constant force, such as centrifugal force, caused by high speed rotation of a continuous-wall spinning head. One example of a mechanism for producing such a combination is a cotton candy making machine. Variations of such an apparatus are contemplated for use in the present invention. The important aspect is that the flash flow phenomena be induced in a solid feedstock for rapid transition to solid, non-flowable thermoplastic material having an altered structure from that of the feedstock.

The term "melt-spinning" has been used in the claims. However, in the context of the present invention "melt-spinning" means subjecting feedstock to the combination of temperature, thermal gradients, mechanical forces, flow, and flow rates during processing which is comparable to that applied to the feedstock during operation of a machine for producing cotton candy. This is in contrast to the use of the term melt spinning in the polymer-processing art. Conventional "melt spinning" is used by the polymer technician to describe processes for extruding polymers which are held under liquid or melted conditions for comparatively long periods of time before being extruded through an orifice.

The present invention also relates to novel solid products obtained by subjecting a thermoplastic polymer and, optionally, additional "guest" materials to flash flow processing.

In accordance with another aspect of the present invention there is provided a method of binding a substance to a thermoplastic polymer from which said substance can escape over a period of time, which includes subjecting a thermoplastic polymer and said substance to flash flow conditions to unite said substance and said polymer.

Other aspects of the present invention involve the production of the novel products which result from carrying out the foregoing methods.

As a result of the present invention, thermoplastic material can be processed efficiently and effectively by a totally unique method to provide new thermoplastic material with new properties in and of itself. Moreover, the new thermoplastic product can be used as a host material to suspend or carry a "guest" material for protection, sustained release, etc.

The invention will be better understood in light of the following detailed description of the preferred embodiments.

DETAILED DESCRIPTION OF THE PREFERRED EMBODIMENTS

It has been discovered that a wide range of thermoplastic polymers can be subjected simultaneously to a combination of heat and shear to provide a host thermoplastic material which has an altered physical structure. The host thermoplastic material is quite useful as a result of characteristics created by flash flow alteration. Moreover, the host thermoplastic material can be a carrier for a guest material such as an active agent. The thermoplastic material will envelop or bind such agents during flash flow alteration to yield a product having various novel characteristics depending on the guest material.

Thus, if a guest agent is normally subject to rapid oxidation when exposed to air, such agent can be isolated from the surrounding air so as to reduce or avoid oxidation. If the guest agent is a fragrance, it can be slowly released over an extended period of time.

Thermoplastic materials which are useful in the present invention can be selected from the classes of thermoplastic polymers. For example, acrylonitritile-butadiene-styrene (or ABS) resins, which are produced by grafting styrene and acrylonitrile onto a diene-rubber backbone, can be used. Artisans prefer polybutadiene as a substrate for ABS polymers. Moreover, ABS plastics are compatible with other plastics, which makes them useful as an additive or modifier for many applications.

Other thermoplastic materials are acetal resins which are also known as polyoxymethylenes, polyacetals, and aldehyde resins. These plastics, which have a wide variety of applications (especially as a metal replacement), are high molecular weight polymers with a basic molecular structure of repeating carbon-oxygen links. The alternating oxymethylene structure, $OCH_2$, provides these thermoplastic materials with a chemistry similar to the simple acetals. Homo- and copolymers are produced based on polymerization of formaldehyde. Due to the high structural strength and resistance to attack by organic compounds, the acetals are quite useful in reducing costs associated with metal parts which are replaced by acetal plastic parts.

Acrylic thermoplastics, other than ABS plastics, include acrylic esters represented by the generic formula $CH_2$=CHC(O)OR. Acrylic monomers readily polymerize or copolymerize with a variety of other monomers. A nonlimiting list of acrylic polymers is as follows: poly (methyl; ethyl; propyl; n-, sec-, iso-, and tert-butyl; hexyl; heptyl; 2-heptyl; 2-ethylhexyl; 2-ethylbutyl; dodecyl; hexadecyl; 2-ethoxyethyl; isobornyl; and cyclohexyl) acrylate. Acrylics tend to serve as permanent plasticizers for harder monomers in a copolymer system. Acrylic polymers and copolymers have greater resistance to both acid and alkaline hydrolyses than do vinyl acetate mono- and copolymers. Acrylics are useful in coating, textiles, cement, ceramics, sealants, films, etc.

Yet another class of thermoplastic material is cellulosics (cellulose nitrate, cellulose acetate, cellulose acetate-propionate and cellulose acetate-butyrate ethyl cellulose, and 2-hydroxypropyl-cellulose). Cellulose itself is the main polysaccharide found in living plants. It forms the skeletal structure of the cell wall, hence the name cellulose. Commercial cellulose are evaluated on the basis of their content of alpha-cellulose. Cellulose derivatives are compounds, typically esters or ethers produced by treating cellulose with various inorganic or organic reagents. The cellulose polymers are semi-synthetic. Ethyl cellulose which is prepared by a reaction of cellulose with alkyl chloride under basic conditions can be used in molding and coating applications. Cellulose propionate has been used for making colored plastics such as telephones, etc. Cellulose xanthate has been spun in the past to produce rayon or has been cast by extrusion to provide cellophane. Methyl cellulose on the other hand has been used as a thickening suspension and stabilizing agent in foods and in nonfood. (Ethyl cellulose has been used for many of the same purposes as methyl cellulose). Hydroxyethylcellulose has also been used as a thickening and suspension agent for food. Carboxymethyl-cellulose has been used as an additive to detergents to prevent redeposition of soil on fabrics.

Yet another thermoplastic material which can be subjected to the inventive process to provide new inventive material is polytetrafluoroethylene (PTFE), a perfluorinated straight-chain polymer having the chemical formula $(CF_2CF_2)_n$. PTFE is a nonflowable solid material. PTFE has been used in a variety of applications, many of which include electrical, mechanical and chemical. For use in the present invention, PTFE can be provided as a granule or as a fine powder. For purposes of the present invention, of course, the flash flow phenomena contemplates the transition from a solid internally-nonflowable material through an internally-flowable stage to a second solid having an altered structure.

Closely related to PTFE are the fluorinated ethylene and propylene polymers and copolymers. Tetrafluorethylene (TFE) and hexafluoropropylene (HFP) can be produced as alternatives to PTFE. The copolymers retain many of the desired properties of PTFE but can be more easily processed in conventional melt processing techniques. The fluorinated ethylenepropylene compounds also have excellent thermostability and chemical inertness while their dielectric constants and dissipation factors are low and remain unchanged when subjected to a wide range of temperature and frequency. Fluorinated ethylene-propylene copolymers (FEP) are available in four materials; low melt viscosity, extrusion grade, high melt viscosity resins and FEP copolymer dispersions. However, the present invention is directed to the transition of a solid thermoplastic feed stock material having no internal flow through a instantaneous internal flow condition to a second solid which has an altered structure.

The next class of thermoplastic materials considered for use herein are the polyamides (usually referred to as nylon). Polyamides can be formed into fibers and can also be used in other thermoplastic applications such as reinforcements for tires and other industrial applications. The polyamides are long-chain synthetic, polymeric amides in which recurring amide groups are integral to the main polymer chain. Nylon-6 and nylon-6,6 comprise about 75–80% of the nylon molding-compound market. In addition to the fiber market referred to above, nylon is used in a large number of automotive and truck components and parts. They have also been used for example in power-tool housings, combs, and bicycle wheels.

Another class of thermoplastics for use in the present invention are the polycarbonates which are a special class of polyesters derived from the reaction of carbonic acid derivatives with aromatic, aliphatic, or mixed diols. The polycarbonate bisphenol A exhibits high hydrolytic stability and excellent thermal stability. In the past, polycarbonates have been used in aeronautics and impact-resistant and electrical products.

Another popular class of thermoplastic materials are the olefin polymers, e.g., polyethylene and polypropylene. For example, linear low density polyethylene (LLDPE) consists of a long sequence of methylene units with periodic uniform short chains. LLDPE has been used in pipe, film, rotational molding, injection molding and wire and cable resins. High pressure low and intermediate density polyethylene on the other hand is a polymer of high molecular weight having a formula $(CH_2CH_2)_n$. Olefin copolymers useful in the thermoplastic industry include poly(ethylene-co-vinyl acetate) (EVA) and poly(ethylene-co-ethyl acrylate) (EEA). Both are random copolymers which possess the advantage of greater flexibility, reduced melting point, and greater capacity for acceptance of fillers. Linear high density polyethylene (HDPE) has a molecular structure of polyethylene or a very high molecular weight alpha olefin, $CH_2=CH(CH_2CH_2)_nH$. The high density polyethylene (HDPE) becomes highly crystalline when cooled below its crystalline freezing point. HDPE has been used in wire and cable insulation, in containers, pipe, housewares, toys, filament, film, etc.

Polypropylene on the other hand is a thermoplastic material which can be polymerized in a crystalline head-to-tail polymer containing essentially an isostatic structure. Polypropylene offers a combination of heat resistance, tensile strength, abrasion resistance, optical gloss and clarity, and low specific density. Thus, it has been found useful for packaging (e.g. sheeting materials), products which must be stretch oriented, such as textile yarns, monofilaments, brushes, straps, ribbons, etc., and pipes for water systems, heating systems, etc.

Inasmuch as most olefins with vinyl double bonds can be polymerized to isotatic polymers, polymers of higher olefins are also considered for use in the present invention. Thus, poly(1-butlyene) can be used as well as other higher carbon-number olefins.

Polystyrene is another thermoplastic material which is used in the present invention. Polystyrene is the parent of the styrene plastics and is a high molecular weight linear polymer having a representative formula $[CH(C_6H_5)CH_2]_n$. Polystyrene is a product family which has as many as 30 members. For example, styrene in butadiene-based rubbers increases impact resistance, and copolymerization of styrene with acrylonitrile products produces heat resistant and solvent-resistant plastics. Polystyrene (and copolymers thereof) is a crystal-clear, hard, rigid thermoplastic which is free of odor and taste. It posseses excellent thermal and electric properties. Isostatic polystyrene, which can be obtained by polymerization with stereo-specific catalysts of the Ziegler-Natta type, has very little commercial use. Antistatic polystyrenes have been developed as styrene-based polymers of alkyls and/or aryl amines, amides, quaternary ammonium compounds, anionics, etc. Acrylonitrile, butadiene, alpha-methyl styrene, methyl methacrylate, and maleic anhydride have copolymerized with styrene to yield commercially significant copolymers. Many latex paints are based on styrene-butadiene copolymers. Methyl methacrylate copolymers with styrene are clear materials which, when stabilized, are similar in light stability to poly (methylmethacrylate). Maleic anhydride copolymers with styrene have alternating structures. Thus, equimolar copolymers are normally produced corresponding to 48 weight percent maleic anhydride. ABS polymers previously discussed herein are two phase systems in which elastomer components are dispersed in the rigid styrene-acrylonitrile (SAN) copolymer matrix. The present invention contemplates the use of styrene polymers and copolymers for processing by use of the flash flow phenomena.

Polyvinylchloride (PVC) is yet another thermoplastic material which is included in the present invention. PVC is produced by free-radical polymerization of vinylchloride and has the structure $[CH_2C(Cl)H]_n$, wherein n can be from 300 to 1500. Addition of the vinylchloride monomer during polymerization can occur in either heat-to-tail fashion or head-to-head or tail-to-tail fashion. PVC has been used in extrusion processes to form sheets, profile extrusion, pipe extrusion, and many other general purpose uses. PVC can also be used in the present invention.

Each of the thermoplastic materials set forth above are included in the present invention. These materials can be and are subjected in the present invention to the flash flow phenomena by which a first non-flowable solid thermoplastic material is subjected to internal flow conditions sufficient to deform and pass through an opening under shear conditions imposed by centrifugal force and instantaneously reform as a second solid material having an altered structure.

Details of the invention have been set forth herein in the form of examples which are described below. The full scope of the invention will be pointed out in the claims which follow the specification.

In each of the following examples, the material is subjected to processing in an Econo Floss machine which has been described hereinbefore in the "Background" portion of the specification. Unless otherwise indicated, the temperature of the heating element in the Econo Floss machine was maintained at one of 284° F. (140.0° C.) at low setting, 390° F. (198.9° C.) at medium setting, and 430° F. (221.1° C.) at high setting. Again, unless otherwise specified, the operating speed of the Econo Floss machine was maintained at about 3800 rpm.

EXAMPLE 1

A sample of polyethylene terephthalate, which was obtained from the Aldrich Chemical Company, was subjected to conditions of elevated temperature and shear in the Econo Floss processing machine, e.g., at a temperature of 200° C. and at a speed of 3600 rpm. The polyethylene terephalate was introduced into the machine as a solid.

The solid was immediately accelerated to the perimeter of the spinning head where it under went flash flow and instantaneously formed a second solid which included both fibrous material and flakes. The new thermoplastic material produced was suitable for use as a new thermoplastic material and as a carrier or host material for a "guest" additive, such as an odor producing material, medicament, etc.

EXAMPLE 2

A sample of 100 gm of nylon 6 obtained from the Aldrich Chemical Company was processed by subjecting it to conditions of temperature and shear sufficient to induce flash flow in the Econo Floss machine. The temperature of the heating element was 200° C.

The new thermoplastic material was a floss. The floss was quite different from the solid nylon 6 which was added to the processing machine. The new thermoplastic material was usable for its own properties, and as a host or carrier for a guest ingredient which may have been selected for a designated purpose.

EXAMPLE 3

A 100 gm sample of cellulose acetate having an acetal content of 39.8% and a molecular weight of 30,000, which was obtained form the Aldrich Chemical Company, was subjected to conditions of temperatures and shear sufficient to induce flash flow in order to produce a new thermoplastic material in the form of a ribbon-like floss.

The new material was completely changed from the structure of the original cellulose acetate, and was quite suitable for use in its altered condition as both a thermoplastic material or as a host material for a guest additive.

EXAMPLE 4

Another sample of thermoplastic material, 100 gm of a polyethylene having a molecular weight of 10,000, and bearing the trade name Epolene N-10 (from Eastman Chemical Company), was subjected to conditions of temperature and shear sufficient to induce flash flow in the Econo Floss machine.

A high quality soft, fluffy floss resulted from the process. The new material was dramatic in its presentation and has been found to be extremely useful for depositing a waxy coating to substrates against which it is rubbed. It is believed that this soft, fluffy floss has a vast number of uses in its altered condition alone or as a carrier for a guest material.

One particularly advantageous feature was demonstrated when the floss was added to an oil-water mixture. The floss absorbed 20 times its own weight of the oil.

EXAMPLE 5

Another 100 gm sample of the Epolene N-10 polyethylene was mixed with 100 gm of sucrose. The mixture was subjected to conditions which induced flash flow. The resulting altered thermoplastic material was a floss which was mixed with 5 gm of the surfactant Igepal (a nonoxynol sold by GAF) and reprocessed through flash flow conditions 5 times.

The resulting material was a high quality soft white floss having a polyethylene host and a surfactant guest material carried therein. The floss was added to water which resulted in a fine colloidal dispersion. Thus, it can be seen that the thermoplastic post material can be modified by guest additives to enhance characteristics such as dispersibility.

EXAMPLE 6

5 gm of styrafoam peanuts obtained from Sigma Chemical Co. of St. Louis, Mo. was mixed with 1 gm of hydroquinone (1/4-benzenediol 99+%), a photographic reducer and developer obtained from the same company, the mixing being accomplished in a food processor operated for about 7 minutes. The mixture was then subjected to flash flow processing in an Econo Floss machine using the 120 volt heating element at high setting. The product produced was a beautiful floss.

A 2 gm sample of the floss was added to 30 cc of tap water and exposed to light. After 24 hours the water took on a light brown color, obviously from the reduction of liberated hydroquinone. This appeared to be a relatively slow process, the hydroquinone being liberated slowly. As spun and during its entire time in water, the floss had a whitish color.

EXAMPLE 7

A 1 gm sample of crystalline hydroquinone, from the same batch used in Example I, was added to 20 cc of tap water. A tan color appeared in about 2 minutes. When floss from Example I was added to water it took about 4 minutes for a tan color to appear. Some of the floss from Example I was also maintained exposed to room atmospheric conditions. The exposed floss remained pure white in appearance for a matter of weeks. However, leaving the unmodified crystals exposed to air causes the crystals to turn brown in about 6 to 12 hours.

EXAMPLE 8

3 gm of material obtained from a styrofoam cup purchased at a local supermarket were mixed in a food processor with 1 gm of Rhodamine B (red dye) obtained from a private laboratory. The mixing was performed with a metal blade first chopping up the cup material for about 5 minutes, after which the Rhodamine B was added with mixing continued for two more minutes.

The mixture was then subjected to flash flow in the Econo Floss machine using the 120 volt heating element at high heat setting. A pink floss was produced which was determined by microscopic examination to consist of the red dye contained within or trapped by the plastic.

A quantity of the pink floss was placed in tap water. After six days the dye was still leaching out of the spun fibers.

EXAMPLE 9

5 gm of tert-butyl hydroquinone from Eastman Kodak company of Rochester, New York, was mixed with 10 gm of diethyl adipate. The mixture was heated for 15 seconds in a microwave oven to produce a uniform solution which was then added to 75 gm of polystyrene powder mol. wt. 45,000, obtained from Wisconsin. The mixture was subjected to flash flow producing a mass of fibers which when pressed together seem to have a degree of roughness.

From the foregoing examples it is apparent that the active agent is isolated to a certain degree from the surrounding environment by the thermoplastic polymer. It is anticipated that the subject invention will simplify the storage of various active agents of which hydroquinone and Rhodamine B are merely examples.

EXAMPLE 10

Isotactic polypropylene obtained from Aldrich Chemical Co., Inc. of Milwaukee, Wis., was subjected to flash flow processing. This was accomplished verifying that polypropylene can be spun, and it spun very well.

EXAMPLE 11

For this example, "Vaseline" petroleum jelly from Chesebrough-Ponds, Inc. was mixed in a metal bladed food processor with isotactic polypropylene obtained from Aldrich Chemical Co., Inc. of Milwaukee, Wis., in the amounts of 10 gm petroleum jelly and 70 gm polypropylene. The mixture was mixed for about 4 minutes and then subjected to flash flow in the Econo Floss machine. A fine textured floss was produced.

A quantity of the floss was placed in a beaker containing "Mazola" corn oil and water. The floss preferentially absorbed the oil. In water alone the floss appeared to be hydrophobic. There was no apparent dissolution of the floss in either the oil or water.

EXAMPLE 12

Into a food processor was placed 15 gm "Vaseline" Petroleum Jelly, 45 gm "Domino" granulated sugar, and 12 gm polypropylene, same as used in Examples 10 and 11. The compositions were mixed for about 5 minutes, then subjected to flash flow with the Econo Floss machine using the 130 volt heating element at the high setting. A fine hydrophobic floss was produced which when added to tap water floats on the surface.

100 gm of Exxon Superflo 10W-40 motor oil was added to a beaker of tap water. A 5 gm ball of the above floss was floated upon the oil surface. After about ten minutes the floss ball, now filled with oil, was retrieved and weighed. The 5 gm ball now weighed 99 gm, essentially 20× its original weight.

EXAMPLE 13

Medium density polyethylene from Aldrich Chemical Co., Inc. was subjected to flash flow by itself producing a magnificent floss. A quantity of the floss was placed in a container containing tap water and "Texaco" 10W-40 motor oil. The floss absorbed up to 25× its own weight of the oil.

Examples 11, 12 and 13 demonstrate the use of the invention for producing an oil spill cleanup material.

EXAMPLE 14

In a glass vessel was mixed 10 gm of tert-Butyl-hydroquinone with 30 gm of poly (methyl methacrylate). The hydroquinone was from Eastman Kodak Company of Rochester, N.Y. and the poly (methyl methacrylate) from Aldrich Chemical Co., Inc. of Milwaukee, Wis. The materials were mixed by hand for about 5 minutes using a glass rod. Then the mixture was subjected to flash flow in the Econo Floss machine. The resulting product was in the form of short filaments, possibly best described as spicules. The color was consistent with the original color of the mixture prior to spinning. A small quantity was placed in a glass beaker with a small amount of tap water. Twelve hours later the water was colored brown evidencing a reduction of the hydroquinone.

From this and the prior examples it should be apparent that the invention provides a novel method of incorporating an active chemical agent within a polymer. The new thermoplastic product is useful both in prolonging the shelf life of the active agent and in providing for slow release and delivery to a fluid environment.

EXAMPLE 15

Into a food processor was placed polystyrene powder from Sigma Chemical Co. and "Charley" Oil from Revlon, in the ratio of 10 parts polymer to 1 part oil. The materials were mixed for about two minutes and then subjected to flash flow conditions in the Econo Floss machine. Beautiful fragrant floss was produced. The floss released fragrance into the surrounding atmosphere over a period of better than 6 months.

EXAMPLE 16

Each of the below numerated thermoplastic polymers were separately mixed with "Mazola" corn oil in the ratio of 10 parts polymer to 1 part corn oil. The compositions were stirred with a glass rod for about 4 minutes, then subjected to flash flow condition with the Econo Floss machine.

a) Polyvinyl alcohol, Mol. Wt. 70,000 b) Polyvinyl acetate, medium Mol. Wt.

c) Poly (acrylic acid), Mol. Wt. 250,000 d) Polyvinyl alcohol, Mol. Wt. 30,000–70,000 e) Poly (methyl methacrylate), Mol. Wt. 12,000

Polymers (a) and (d) were obtained from Sigma Chemical Co., while polymers (b), (c) and (e) were obtained from Aldrich Chemical Co., Inc.

In the case of polymers (a), (b), (c) and (d), the new thermoplastic product was a high quality floss fiber entrapping the oil which is released at an extremely slow rate. The poly(methyl methacrylate) resulted in a new thermoplastic material which appeared as short truncated fibers, also entrapping oil.

EXAMPLE 17

Medium density polyethylene from Aldrich Chemical Co., Inc. was prepared with "Mazola" corn oil following the same procedure set forth in Example 16. An attractive, exquisitely textured floss was produced which resembled surgical cotton. Oil leaches from the spun product at a very slow rate.

EXAMPLE 18

Medium density polyethylene, 5 parts by weight, from Aldrich Chemical Co., Inc. was mixed with 1 part cedar wood oil from Sigma Chemical Co. The mixture was subjected flash flow conditions in the Econo Floss machine producing a beautiful cottony floss with a strong cedar smell. The floss is useful as an odorizer or the like. After six months the unique thermoplastic product still delivers a cedar odor.

EXAMPLE 19

Low, medium and high density polyethylene from Aldrich Chemical Co., Inc. were each separately processed with the Econo Floss machine producing, respectively, a course floss, a very fine floss, and a short truncated fiber or spicule.

EXAMPLE 20

2.5 gm of Poly R478, Poly (vinylamine sulfonate), a polymeric dye from Sigma Chemical Co., was mixed with 25 gm polystyrene, mol. wt. 45,000, from Aldrich Chemical Co., Inc. After 4 minutes of hand mixing the mixture was subjected to flash flow conditions with the Econo Floss machine. The product was a floss with a beautiful purple color.

0.25 gm of this floss was put in a glass beaker with 40 cc. of tap water. Within 4 hours the water had turned purple. Each day for 30 consecutive days (except Saturdays and Sundays) the water was decanted, the floss was rinsed in clean water, and then rinsed floss was placed in a clean beaker with 40 cc of fresh water. After 30 days the water was still turning purple. Thus, the present invention provided a controlled release thermoplastic product.

EXAMPLE 21

10% by weight of "Triaminic-DM" produced by Dorsey Laboratories Div. of Sandoz, Inc. of Lincoln, Nebr. was mixed with 90% by weight of medium density of polyethylene powder. "Triaminic-DM" is specified by its manufacturer as containing in each 5 ml does, 12.5 mg phenyl propanolamine hydrochloride, 10 mg dextro methorphan hydrobromide with benzoic acid, blue No. 1, flavors, propyline glycol, purified water, red 40, sodium chloride, sorbitol and sucrose. The mixture was subjected to flash flow conditions using the Econo Floss machine and a beautiful floss was produced. The floss had a uniform red color corresponding to the color of the drug.

The floss was placed in 30 ml of tap water. After 1 hour the water was red. The experimenter drank the water and within 15 minutes reported a definite antihistaminic effect clearing existing allergy symptoms. Evidently, the antihistaminic medication passed through the spinning process without degradation and was entrapped within or by the thermoplastic polymer. However, exposing the resultant floss to water served to release the antihistamine. This process can be used to store a medicament for subsequent slow release. A product produced by this process can be implanted in body tissue, or incorporated in a topical patch or dressing.

EXAMPLE 22

A family of polymers were used for this example. They are marketed by Dupont Company of Wilmington, Del. under the "MEDISORB" trademark and are generically identified as a "Lactide/Glycolide Polymer" containing "Propanoic Acid, 2-Hydroxy-Polymer with Hydroxyacetic Acid." Four such polymers were used, namely:

a) Lactide/Glycolide 100L. This is believed to be 100% Lactide having a melting point within the range of 338°–347° F. (170°–175° C.);

b) Lactide/Glycolide 100DL. This is believed to be 100% Glycolide having a melting point within the range of 437°–455° F. (225°–235° C.);

c) Lactide/Glycolide 85 15DL. This is believed to be a copolymer containing 85% Lactide and 15% Glycolide with a melting point within the range of 338°–347° F. (170°–175° C.); and d) Lactide/glycolide 50 50DL. This is believed to be a copolymer containing 50% Lactide and 50% Glycolide with a melting point within the range of 338°–347° F. (170°–175° C.).

Each of the above polymers was mixed with 15% by weight of "Mazola" corn oil and then subjected to flash flow with the Econo Floss machine. The resultant product was somewhat ribbon-like with some fibrous elements present. The oil was released over a period in excess of two weeks. Each day the floss was rinsed and dried carefully. By the following day the floss was very oily to the touch. Evidently the oil migrated to the surface.

Having described the present invention with reference to numerous examples, it is to be understood that any thermoplastic polymer that can be subjected to melt spinning as defined herein without being degraded, burnt or otherwise damaged, can be used as the carrier for another ingredient or active agent. Melt spinning a mixture of such polymer and an active agent produces a trapped form of said active agent which isolates the active agent from its surroundings yet permits slow release in the appropriate fluid environment. The principal limitation upon carrier or active agent is that neither be degraded while being melt spun. Also, the carrier and active agent should be chemically compatible.

Thus, while there have been disclosed what are presently believed to be the preferred embodiments of the present invention, other and further manifestations of the invention will become apparent to those skilled in the art, and it is inteded to claim all such changes and modifications as come within the true scope of the present invention.

I claim:

1. A method of producing a solid thermoplastic-containing matrix wherein said method comprises subjecting a solid feedstock comprising a thermoplastic polymer to flash flow melt spinning wherein said melt spinning is conducted at a temperature of about 200–430° F. and shear imposed by centrifugal force from an operating speed of about 3600 to about 3800 revolutions per minute, thereby causing transition of said thermoplastic polymer from a solid having no internal flow to a second solid being in matrix form selected from the group consisting of a floss, fiber, flake, filament, ribbon, spicule, and mixtures thereof.

2. A method according to claim 1, wherein said thermoplastic polymer is selected from the group consisting of polypropylene, polystyrene, polyethylene, polyvinylacetate, polyvinylalcohol, poly(methyl methacrylate), polyacrylic resin, lactide/glycolide copolymer, and combinations thereof.

3. A method according to claim 1, wherein said feedstock further includes a guest material.

4. A method according to claim 3, wherein said thermoplastic polymer is polystyrene.

5. A method according to claim 3, wherein said guest material is selected from the group consisting of a colorant, an odor-producing substance, a comestible, an oleaginous material, a photographic reducer and developer, an organism and, an antioxidant.

6. A method according to claim 5, wherein said colorant is a polymeric dye.

7. A method according to claim 5, wherein said colorant is selected from the group consisting of Rhodamine B and polyvinylamine sulfonate.

8. A method according to claim 5, wherein said odor-producing substance is cedar wood oil.

9. A method according to claim 5, wherein said oleaginous material is selected from the group consisting of petrolatum, vegetable oil and fragrant oil.

10. A method according to claim 1, wherein said transition occurs in not more than 1.0 second.

11. A method according to claim 10, wherein said transition occurs in not more than 0.4 second.

12. A method according to claim 10, wherein said transition occurs in not more than 0.1 second.

13. A method of binding a guest material to a thermoplastic polymer from which said guest material can escape, wherein said method comprises subjecting said thermoplastic polymer and said guest material to flash flow melt spinning wherein said melt spinning is conducted at a temperature of about 200–430° F. and shear imposed by centrifugal force from an operating speed of about 3600 to about 3800 revolutions per minute, thereby uniting said guest material and said polymer to produce a solid thermoplastic matrix containing said guest material, said matrix being in a form selected from the group consisting of floss, fiber, flake, filament, ribbon, spicule, and mixtures thereof.

14. A method according to claim 13, wherein said guest material is selected from the group consisting of a colorant, an odor-producing substance, a comestible, an oleaginous material, a photographic reducer and developer, an organism and, an antioxidant.

15. A method according to claim 14, wherein said photographic reducer and developer is a hydroquinone.

16. A method according to claim 14, wherein said organism is a unicellular organism.

17. A method according to claim 13, wherein said thermoplastic polymer is present in an amount greater than said guest material on a weight basis.

18. A method according to claim 17, wherein said thermoplastic polymer is present in an amount at least about 50% greater than said guest material on a weight basis.

19. A new thermoplastic material comprising a host thermoplastic product prepared by subjecting a solid feedstock comprising a thermoplastic polymer to flash flow melt spinning wherein said melt spinning is conducted at a temperature of about 200–430° F. and shear imposed by centrifugal force from an operating speed of about 3600 to about 3800 revolutions per minute, thereby causing transition of said thermoplastic polymer from a solid having no internal flow to a second solid being in a form selected from the group consisting of a floss, fiber, flake, filament, ribbon, spicule, and mixtures thereof.

20. The thermoplastic material of claim 19, wherein said thermoplastic polymer is selected from the group consisting of acrylonitrile-butadiene-styrene resins; acetals, acrylics; cellulosics; chlorinated polyethers; fluorocarbons; nylons; polyamides; polycarbonates; polyethylene polymers and copolymers; polypropylene polymers and copolymers; polystyrenes; vinyls; and combinations thereof.

21. The thermoplastic material of claim 19 wherein said feedstock includes a guest material.

22. The thermoplastic material of claim 21 wherein said thermoplastic polymer is polystyrene.

23. The thermoplastic material of claim 21, wherein said guest material is selected from the group consisting of a colorant, an odor-producing substance, a comestible, an oleaginous material, a photographic reducer and developer, an organism and, an antioxidant.

24. The thermoplastic material of claim 23, wherein said colorant is a polymeric dye.

25. The thermoplastic material of claim 23, wherein said colorant is selected from the group consisting of Rhodamine B and polyvinyl sulfonate.

26. The thermoplastic material of claim 23, wherein said odor-producing substance is an oil.

27. The thermoplastic material of claim 26, wherein said odor-producing substance is selected from the group consisting of essential oils, wood oil and fragrance oil.

28. The thermoplastic material of claim 23, wherein said photographic reducer and developer is a hydroquinone.

29. The thermoplastic material of claim 23, wherein said organism is a unicellular organism.

* * * * *